United States Patent [19]

Kanai et al.

[11] Patent Number: 4,962,245
[45] Date of Patent: Oct. 9, 1990

[54] PROCESS FOR PREPARING HALOGENATED BENZENE DERIVATIVES

[75] Inventors: Takashi Kanai; Michio Kimura; Yoshio Noguchi, all of Aichi, Japan

[73] Assignee: Toray Industries, Japan

[21] Appl. No.: 313,074

[22] Filed: Feb. 21, 1989

[30] Foreign Application Priority Data

Feb. 26, 1988 [JP] Japan .................................. 63-44934

[51] Int. Cl.$^5$ .............................................. C07C 17/37
[52] U.S. Cl. ..................................... 570/211; 570/202
[58] Field of Search ............................... 570/202, 211

[56] References Cited

U.S. PATENT DOCUMENTS

| | | | |
|---|---|---|---|
| 4,254,062 | 3/1981 | Wambach et al. | 570/211 |
| 4,650,915 | 3/1987 | Arpe et al. | 570/211 |
| 4,774,371 | 9/1988 | Miwa et al. | |
| 4,777,306 | 10/1988 | Kaneshiki et al. | 570/211 |
| 4,814,526 | 3/1989 | Rule et al. | 570/211 |

Primary Examiner—Werren B. Lone
Attorney, Agent, or Firm—Austin R. Miller

[57] ABSTRACT

By a process for preparing halogenated benzene derivatives comprising distilling or stripping a mixture of the isomers of a halogenated benzene derivative containing a hydrogen halide to remove the hydrogen halide from the isomeric mixture of the halogenated benzene derivative and then contacting with a zeolite adsorbent for selectivity separating the desired isomer of the halogenated benzene derivative, it is possible to prevent from degrading the zeolite adsorbent. And it is possible to separate selectively industrially an desired isomer of the halogenated benzene derivative for a long time without reduction of productivity and to separate selectively the desired isomer in high purity.

13 Claims, 1 Drawing Sheet

PROCESS FOR PREPARING HALOGENATED BENZENE DERIVATIVES

BACKGROUND OF THE INVENTION (1) Field of the Invention

This invention relates to a process for preparing halogenated benzene derivatives by adsorptive separation.

(2) Description of the Prior Art

Halogenated benzene derivatives typically include dichlorobenzene, chlorotoluene, dichlorotoluene and dichlorocumene, and these are important as intermediates for synthesis of agricultural chemicals and medicines.

A halogenated benzene derivative is generally obtainable as a mixture of isomers through halogenation of benzene, alkyl benzene or halogenated alkyl benzene and is provided by isolating the desired isomer from such mixture of isomers. Separation of the isomer is generally made by distillation, crystallization or adsorption. But, as these isomers are not much different in boiling or freezing point, a conventional distillation or crystallization method is hardly applicable.

On the other hand, there have recently been developed methods of isomerizing a dialkylbenzene such as xylene in the presence of a catalyst (U.S. Pat. No. 4,409,413) and a method of adsorptive separation of a mixture of alkylbenzene isomers with a zeolite adsorbent (Japanese Examined Patent Publication No. 15681/1977 and Japanese Examined Patent Publication No. 38202/1983). According to these methods, the desired isomer is obtainable at a considerable purity. Further, by feeding the remaining components after separation to an isomerization process and thus isomerizing them, and then separating the desired isomer in adsorptive separation once more, it is possible to ultimately produce the desired isomer only.

However, when said method of isomerization and adsorption separation is applied to production of halogenated benzene derivatives, degradation of the zeolite adsorbent occurs gradually, resulting in reduction of productivity.

SUMMARY OF THE INVENTION

The inventors looked into the cause of degradation of the zeolite adsorbent and found that a very small amount of hydrogen halide contained in the material and a very small amount of water cause degradation of the zeolite adsorbent.

Further, the inventors found that zeolite adsorbent of the water absorbing type, such as faujasite type zeolite, are degraded to a considerable extent.

Moreover, the inventors found that the zeolite adsorbent is deteriorated by the co-presence of water and hydrogen halide a high concentration in the material to be adsorbed, and degraded the adsorbing capacity.

Therefore, the inventors found that it is required to suppress the water content in the material to be adsorbed as far as practicable, and that it is possible to prevent degradation of the zeolite adsorbent.

An object of the present invention is to provide, in contacting a mixture of the isomers of halogenated benzene derivatives containing hydrogen halide with a zeolite adsorbent and, thus, selectively separating the desired isomer of the halogenated benzene derivative, a process of preventing degradation of the zeolite adsorbent by selectively separating industrially a desired isomer of the halogenated benzene derivative for a long time without reduction of productivity.

Another object of the present invention is to provide a process of contacting a mixture of isomers of a halogenated benzene derivative containing a hydrogen halide with a zeolite adsorbent and, thus, selectively separating the desired isomer in high purity.

Other and further objects, features and advantages of the invention will appear from the following description.

These objects are attained by process for producing halogenated benzene derivatives comprising distilling or stripping a mixture of the isomers of a halogenated benzene derivative containing a hydrogen halide to remove the hydrogen halide from the isomeric mixture of the halogenated benzene derivative and then contacting with a zeolite adsorbent for selectivity separating the desired isomer of the halogenated benzene derivative.

DETAILED DESCRIPTION OF THE PREFERRED EMBODIMENTS

Figure 1:
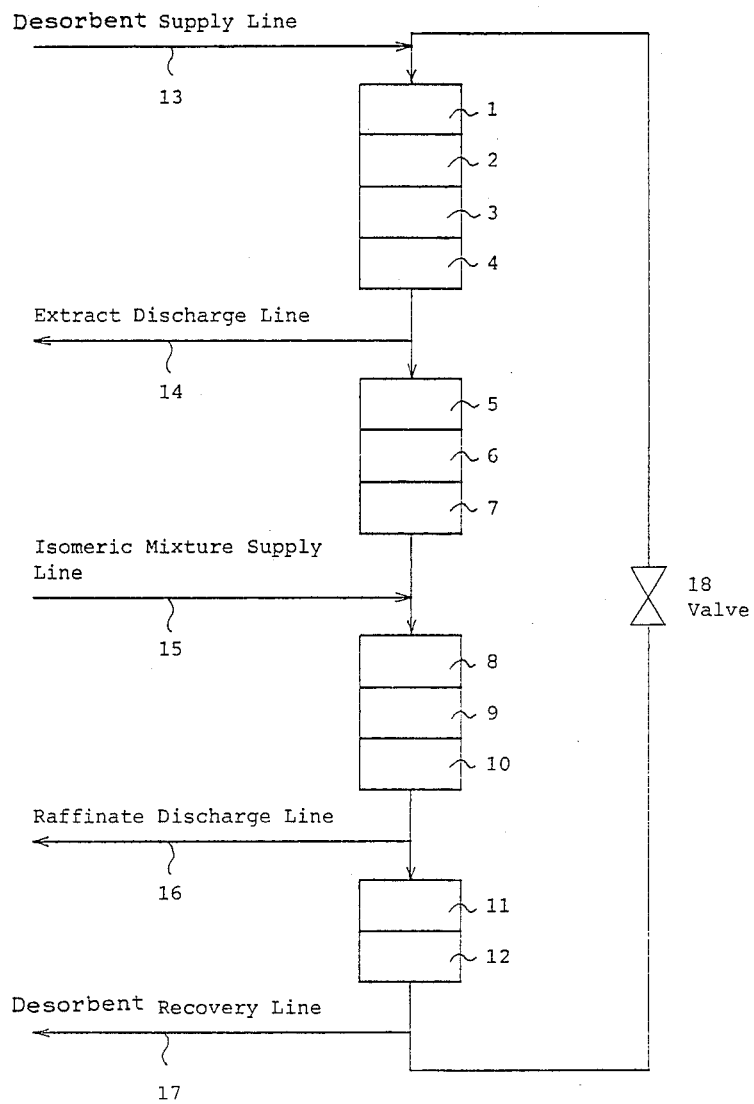
FIG. 1 is a flow diagram illustrating continuous adsorptive separation of a dichlorobenzene isomer using a simulated moving bed.

For the halogenated benzene derivative used as a starting material according to the method of the invention, for example, there by be cited compounds expressed by the following general formula (I):

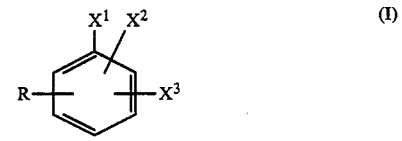

wherein $X^1$ represents a halogen atom, $X^2$ and $X^3$ a haolgen or hydrogen atom, and R a lower alkyl group or halogen atom.

Here, R is a lower alkyl group and shows an alkyl group of 1 to 4 carbon atoms. Specifically, there may be listed a methyl group, ethyl group, n-propyl group, iso-propyl group, n-butyl group, sec-butyl group, and tert-butyl group. When $X^1$, $X^2$, $X^3$ or R represents a halogen atom, the halogen atom may be the same or different. Specifically, the halogen atom includes chlorine, bromine and iodine atom, preferably chlorine and bromine. Halogenated benzene derivatives include, for example, dichlorobenzene, chlorotoluene, dichlorotoluene, trichlorobenzene, trichlorotoluene, tetrachlorobenzene, dibromobenzene, bromotoluene, dibromotoluene, dichlorobromobenzene, tribromobenzene, dibromochlorobenzene, chlorocumene, dichlorocumene, trichlorocumene, dibromocumene and bromocumene. Of these, chlorobenzene, chlorotoluene, dichlorotoluene and dichlorocumene are preferable. These halogenated benzene derivatives are respectively supplied as a mixture of isomers.

The mixture of isomers of a halogenated benzene derivative used as a material according to the method of the invention is normally provided by halogenation reaction of benzene, alkylbenzene or halogenated alkyl benzene, or isomerization reaction, and contains a very small amount of a hydrogen halide as a by-product. The isomer mixture of halogenated benzene derivative usually contains a small amount of water.

The halogenation reaction or the isomerization reaction may be carried out by a conventional method.

For example, the isomerization reaction is carried out by contacting a starting material, such as a mixture of isomers of a halogenated benzene derivative, with a catalyst. Here, as a catalyst, aluminum trichloride or zeolite is usable. Specific examples of zeolite catalyst, a faujasite type zeolite, pentasil type zeolite and mordenite type zeolite may be listed. When a zeolite catalyst is used for isomerization, the isomerization may be effected according to Unexamined Japanese Patent Publication No. 144330/1983. That is, any system of gas phase reaction, such as liquid phase reaction, fixed bed, moving bed or fluidized bed are usable under the conditions of a reaction temperature of 200° to 550° C., preferably 250° to 500° C., and a weight hourly space velocity (WHSV) of 0.05 to 30 hours$^{-1}$, preferably 0.1 to 20 hours$^{-1}$.

In the method of the invention, it is important that the mixture of isomers of a halogenated benzene derivative containing a hydrogen halide is subjected to a distillation or stripping treatment for removal of the hydrogen halide.

Absorption with an aqueous alkaline solution that is a conventional method for removal of the hydrogen halide is not preferable in that the isomeric mixture of halogenated benzene derivative unavoidably comes into contact with water and thus has a very small amount of water dissolved, which in turn causes degradation of the zeolite adsorbent used in the subsequent process.

The distillation or stripping treatment enables removal of the hydrogen halide without contact with water.

The isomeric mixture of the halogenated benzene derivative to be subjected to the distillation or stripping treatment is not restricted, and may be the isomerization reaction mixture itself or the extracted or distilled halogenated benzene derivative.

In the method of the invention, the stripping treatment refers to blowing an inert gas suh as N$_2$ into the reaction liquid containing a hydrogen halide to remove hydrogen halide, water and volatile components from the reaction liquid. The distillation treatment refers to the distillation process carried out according to a conventional method.

The distillation or stripping treatment is practicable either by a plate tower or by a packed tower. The operation may be under atmospheric, vacuum or increased pressure. The distillation or stripping treatment is carried out until the concentration of the hydrogen halide in the reaction liquid is reduced to 10 ppm or less, preferably 1 ppm or less.

In the process of the invention, water present in the material is also simultaneously removed by the distillation or stripping treatment.

The distillation or stripping treatment is carried out until the water content is the reaction liquid is reduced to 10 ppm or less, preferably 1 ppm or less.

If the isomerization of a halogenated benzene derivative involves side reactions such as transalkylation, dehalogenation and/or demethylation, there are produced demethylated and/or dehalogenated low boiling components as by-products. For example, when chlorotoluene is isomerized, toluene and chlorobenzene are incidentally produced, each in a very small amount. Such low boiling components scarcely degrade the zeolite adsorbent. But, when a high purity product is required, the low boiling components should be removed. Here, by the distillation or stripping treatment, the low boiling components can be simultaneously removed. When the low boiling components are of a small relative volatility, a multi-stage distillation or stripping tower should be used.

The isomeric mixture of halogenated benzene derivative subjected to the distillation or stripping treatment is fed to a process of adsorptive separation, and in the adsorptive separation process, the desired isomer of the halogenated benzene derivative is selectively separated.

For the adsorbent, a zeolite is usable. These is no particular restriction of the zeolite adsorbent, but those zeolite adsorbents which are subject to great degradation by hydrogen halides provide particularly good results. Specifically, the most preferably result can be obtained, when such zeolites as X types, Y type and other faujasite type zeolites, pentasil type zeolites such as ZSM-5, mordenite type zeolites, L types zeolites and beta type zeolites are used.

As a desorbent, toluene, xylene and other aromatic compound are usable. For adsorption and desorption, ordinary methods and conditions may be employed. For example, adsorption and desorption may be made according to the method in Japanese Examined Patent Publication No. 24981/1988.

The mixture of isomers after adsorptive separation of the desired isomer may be subjected to an isomerization reaction to enhance the concentration of the desired isomer to an equilibrium rate. By such recycling, the desired isomer can be industrially advantageously produced.

The invention will be more clearly understood as it is described with reference to the following examples.

EXAMPLE 1

An aqueous mixture comprising 135 g of sodium silicate, 8.6 g of Al$_2$(SO$_4$) 18H$_2$O, 15 g of n-propylamine, 11.2 g of H$_2$SO$_4$ and 400 g of water was maintained 155° C. for 72 hours for crystallization, and thus there was produced a powder of Zeolite ZSM-5 of SiO$_2$/Al$_2$O$_3$ molar ratio of 45.5 mol/mol. This ZSM-5 powder was subjected to ion exchange for five times with a 10% by weight aqueous solution of ammonium chloride used (solid/liquid ratio, 2.0 l/kg at about 90° C.), then thoroughly rinsed, dried at 120° C. for 15 hours and calcined at 600° C. for 2 hours in air, and there was obtained and acid type ZSM-5 catalyst.

Using the acid type ZSM-5 catalyst thus obtained, and employing a fixed bed flow reactor, isomerization of o-dichlorobenzene was carried out in a liquid phase, and there was obtained a mixture of isomers of dichlorobenzene containing hydrogen chloride. o-Dichlorobenzene was dehydrated with a moleculate sieve. The conditions for isomerization are shown below.
WHSV=4.5 hour$^{-1}$
Reaction temperature=300° C.
Reaction pressure=30 kg/cm$^2$G After the reaction, the composition of the mixture of isomers was o-dichlorobenzene:m-dichlorobenzene:p-dichlorobenzene=58:27:15, and the concentration of hydrogen chloride was 20 ppm, and water was 10 ppm. The concentration of the by-product chlorobenzene was 0.09% by weight.

The obtained reaction mixture was distilled at 200 mmHg for about 30 minutes to remove hydrogen chloride and water from the reaction mixture. After distillation, the hydrogen chloride in the reaction mixture was 1 ppm, water 6 ppm and low boiling components 0.01% by weight. This isomeric mixture was subjected to adsorptive separation by the simulated moving bed system shown in FIG. 1.

The system shown in FIG. 1 will now be briefly described.

To the adsorption chambers 1 through 12, each of an inner capacity of about 13 ml, and X type zeolite adsorbent represented by 0.75 LiO$_2$.0.25Na$_2$O.Al$_2$O$_3$.2.5SiO$_2$ (hereinafter referred to as "Li-X type zeolite") was charged. Through the line 13, the desorbent, toluene, was fed at 300 ml/hr, and though the line 15, said mixture of isomers was fed at 17 ml/hr. Through the line 14, the extract flow was discharged at 74 ml/hr, and through the line 16, the raffinate flow was discharged at 29 ml/hr. The remaining liquid was discharged through the line 17. Flow of the liquid between the adsorption chambers 1 and 12 is closed by a valve 18. Then, the adsorption chamber 1 was shifted to the position of the adsorption chamber 12, the chamber 11 to 10, 8 to 7 and 5 to 4 respectively, at an interval of about 150 seconds (the other chambers being also shifted upward by one chamber simultaneously). The adsorption temperature was 130° C.

At two hours after the start of adsorptive separation, the purity of m-dichlorobenzene in the mixture of isomers of dichlorobenzene contained in the raffinate flow was 99.5%, and the recovery rate of m-dichlorobenzene was 70%. Further, preserving the raffinate flow and extract flow, the composition after 100 hours was examined, and the purity of the product, m-dichlorobenzene in the dichlorobenzene mixture in the raffinate flow, was 99.5%, and the recovery rate was 68%.

EXAMPLE 2

Isomerization and adsorptive separation were carried out as in Example 1, except that instead of distillating the reaction mixture, N$_2$ gas was bubbled in the reaction mixture at about 1 l/min for about 1 hour under room temperature and atmospheric pressure to strip hydrogen chloride and water and thus remove them. After stripping, the concentrations of hydrogen chloride, water and low boiling components in the reaction mixture were 8 ppm, 7 ppm and 0.08% by weight, respectively.

The purity of the product, m-dichlorobenzene in the raffinate flow at 2 hours after start of the adsorptive separation, was 99.6%, and the recovery rate of the product, m-dichlorobenzene was 68%. After 100 hours, the purity of the product, m-dichlorobenzene in the raffinate flow was 99.6%, and recovery rate was 67%.

COMPARATIVE EXAMPLE 1

Isomerization and adsorptive separations were carried out as in Example 1 except that the reaction mixture was not distilled but was directly fed to the process of adsorptive separation.

In the reaction mixture, the hydrogen chloride was 120 ppm, water 10 ppm and low boiling components were 0.09% by weight. The product, m-dichlorobenzene in the raffinate flow at 2 hours after start of the adsorptive separation, was of 99.5% purity and had a recovery rate 68%. After 48 hours, the purity of the product, m-dichlorobenzene in the raffinate flow was 91.3% and the recovery rate was 60%.

EXAMPLE 3

With 2,5-dichlorotoluene used in place of o-dichlorobenzene, and with an X type zeolite substituted by Ag used in place of Li-X type zeolite in Example 1, isomerization, distillation and adsorptive separations were carried out as in Example 1. The product, 2,6-dichlorotoluene, was obtained. The results are shown in Table 1.

Isomerization and adsorptive separations were carried out as in Example 3 except that the reaction mixture was not distilled but directly fed to the process of adsorptive separation. The results are shown in Table 1 as Comparative Example 2.

EXAMPLE 4

With 2,4-dichlorocumene used in place of o-dichlorobenzene and wity Y type zeolite substituted by K used in place of Li-X type zeolite in Example 1, isomerization, distillation and adsorptive separations were carried out as in Example 1. The product, 3,5-dichlorocumene, was obtained. The results are shown in Table 1.

Isomerization and adsorptive separations were carried out as in Example 4, except that the reaction mixture was not distilled but was directly fed to the process of adsorptive separation. The results are shown in Table 1 as Comparative Example 3.

TABLE 1

| | Halogenated Benzene Derivatives | After Reaction | | After Distillation or stripping | |
|---|---|---|---|---|---|
| | | Hydrogen Chloride (ppm) | Water (ppm) | Hydrogen Chloride (ppm) | Water (ppm) |
| Example 1 | Dichlorobenzene | 120 | 10 | 1 | 6 |
| Example 2 | Dichlorobenzene | 120 | 10 | 8 | 7 |
| Comparative Example 1 | Dichlorobenzene | 120 | 10 | — | — |
| Example 3 | Dichlorotoluene | 2500 | 20 | 5 | 4 |
| Comparative Example 2 | Dichlorotoluene | 2500 | 20 | — | — |
| Example 4 | Dichlorocumene | 3500 | 150 | 6 | 10 |
| Comparative Example 3 | Dichlorocumene | 3500 | 150 | — | — |

| | At 2 Hours After Separation | | At 100 Hours After Separation (*) | |
|---|---|---|---|---|
| | Purity of Product (%) | Recovery Rate (%) | Purity of Product (%) | Recovery Rate (%) |
| Example 1 | 99.5 | 70 | 99.5 | 68 |
| Example 2 | 99.6 | 68 | 99.6 | 67 |
| Comparative Example 1 | 99.5 | 68 | 91.3 | 60 |
| Example 3 | 99.7 | 95 | 99.7 | 94 |
| Comparative Example 2 | 99.5 | 87 | 98.1 | 65 |
| Example 4 | 99.4 | 90 | 99.4 | 90 |
| Comparative Example | 97.5 | 82 | 96.3 | 52 |

TABLE 1-continued

3

(*)Concerning Comparative Examples 1, 2, and 3, the purity and recovery rate are the data at 48 hours after separation, not at 100 hours after separation.

What we claim is:

1. A process for separating an isomer of a ring-halogenated benzene derivative having a mono benzene ring from a mixture of the isomers of a ring-halogenated benzene derivative containing hydrogen halide and obtained through isomerization comprising subjecting said mixture to (a) a step selected from distilling and stripping to remove the hydrogen halide therefrom, and then (b) a step of contacting with a zeolite adsorbent for selectively separating the desired isomer of the ring-halogenated benzene derivative.

2. A process according to claim 1, wherein said ring-halogenated benzene is a compound represented by the following general formula (I):

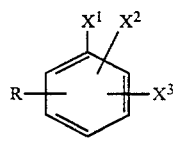
(I)

wherein $X^1$ represents a halogen atom, $X^2$ is selected from a halogen and a hydrogen atom, $X^3$ is selected from a halogen and a hydrogen atom, and R is selected from a halogen atom and an alkyl group having 1 to 4 carbon atoms.

3. A process according to claim 1, wherein said zeolite adsorbent is selected from the group consisting of mordenite zeolites, pentasil zeolites, faujasite zeolites, L zeolites and beta zeolites.

4. The process according to claim 1 wherein said inert gas is blown into said mixture at room temperature.

5. A process for separating an isomer of a ring-halogenated benzene derivative having a mono benzene ring from a mixture of the isomers of a ring-halogenated benzene derivative containing hydrogen halide and obtained through isomerization comprising subjecting said mixture to (a) stripping said hydrogen halide, water and volatile components from said mixture by blowing an inert gas into said mixture, and then (b) contacting the remaining mixture with a zeolite adsorbent for selectively separating the desired isomer of the ring-halogenated benzene derivative.

6. The process according to claim 5 wherein said inert gas is nitrogen.

7. The process according to claim 5 wherein said stripping step is carried out until the concentration of said hydrogen halide in said mixture is 10 parts per million or less.

8. The process according to claim 5 wherein said stripping step is carried out until the concentration of said hydrogen halide in said mixture is 1 part per million or less.

9. The process according to claim 5 wherein said stripping step is carried out until the water content in said mixture is 10 parts per million or less.

10. The process according to claim 5 wherein said stripping step is carried out until the water content in said mixture is 1 part per million or less.

11. The process according to claim 5 wherein about 1 liter per minute of said inert gas is blown into said mixture.

12. The process according to claim 5 wherein said inert gas is blown into said mixture for about an hour.

13. The process according to claim 5 wherein said inert gas is blown into said mixture at atmospheric pressure.

* * * * *